US009017266B2

(12) United States Patent
Leung et al.

(10) Patent No.: US 9,017,266 B2

(45) Date of Patent: Apr. 28, 2015

(54) AUTOMATED TESTING FOR PALPATING DIABETIC FOOT PATIENT

(75) Inventors: Woon Fong Wallace Leung, Kowloon (HK); Kin Tak Alan Lau, Kowloon (HK)

(73) Assignee: The Hong Kong Polytechnic University, Hung Hom, Kowloon (HK)

( * ) Notice: Subject to any disclaimer, the term of this patent is extended or adjusted under 35 U.S.C. 154(b) by 408 days.

(21) Appl. No.: 11/705,522

(22) Filed: Feb. 13, 2007

(65) Prior Publication Data

US 2008/0193905 A1 Aug. 14, 2008

(51) Int. Cl.

| | |
|---|---|
| ***A61B 19/00*** | (2006.01) |
| ***A61B 5/00*** | (2006.01) |
| ***B25J 11/00*** | (2006.01) |
| ***G09B 23/28*** | (2006.01) |
| ***G09B 23/30*** | (2006.01) |

(52) U.S. Cl.

CPC ................ *B25J 11/00* (2013.01); *G09B 23/28* (2013.01); *G09B 23/30* (2013.01)

(58) Field of Classification Search

USPC .................. 600/552, 553, 554, 557, 587, 595

See application file for complete search history.

(56) References Cited

U.S. PATENT DOCUMENTS

| | | | | |
|---|---|---|---|---|
| 4,313,446 | A | 2/1982 | Kanatani | |
| 5,433,211 | A * | 7/1995 | Brammer et al. | 600/552 |
| 5,533,514 | A * | 7/1996 | Lavigne et al. | 600/557 |
| 5,540,235 | A * | 7/1996 | Wilson | 600/554 |
| 5,823,969 | A | 10/1998 | Christy | |
| 6,190,334 | B1 * | 2/2001 | Lasky et al. | 600/587 |
| 6,234,977 | B1 | 5/2001 | Christy | |
| 7,662,113 | B2 * | 2/2010 | Pearl et al. | 600/587 |
| 2006/0178596 | A1 * | 8/2006 | Robichaud et al. | 600/553 |

* cited by examiner

*Primary Examiner* — Brian Szmal

*Assistant Examiner* — H. Q. Nguyen

(74) *Attorney, Agent, or Firm* — Duane Morris LLP; Siegfried JW Ruppert

(57) ABSTRACT

The present invention teaches a system for the automated palpation testing of a patient, including the use of a robotic device with a actuating element thereto. The system is useful for testing patients at risk of nerve degradation, such as diabetic sufferers. The system includes a controller for programming the robotic device to administer the test in a particular pattern, and a storage medium for storing the results of the test. The system allows a more accurate determination of the stage of nerve degradation, as well as being more standardized because of the inclusion of automation technology.

25 Claims, 5 Drawing Sheets

AUTOMATED TESTING FOR PALPATING DIABETIC FOOT PATIENT

BACKGROUND

Examination of the feet of diabetic patients is often the most neglected aspect of clinical diabetic examination. Ulcers secondary to neuropathy tend to occur on the plantar aspect of the feet under areas of high plantar pressure, while ischemeic ulcers tend to affect the toes and dorsum of the foot. Due to loss of nerve and sensation from neuropathy, stresses from loading exerted on the soft tissues between the hard bones and callus at the planter of the foot tend to wear out the soft tissues leading to ulcers and possible amputation of the foot of portion thereof under serious situation. Therefore, it is important to detect neuropathy before developing into serious ulcers for diabetic patients. A wide variety of techniques are used to assess neurological integrity on diabetic sufferer's feet, including tuning fork and monofilament testing.

Filament testing has long been used as a sensitive monitoring means for evaluating peripheral nerve function of a patient. In the 1800's, the focus of peripheral nerve testing of the hands was carried out in a study of normal physiology using horse hairs as the filaments. In the late 1950's, it was determined that a broader range of filament forces were needed than those available with horse hairs to refine the filament method for peripheral nerve testing. Thus J. Semmes and S. Weinstein developed and published results of testing cutaneous sensory perception using nylon monofilament rods of varied diameters and consistent tips, and further published methods of using those rods to apply force. The nylon filaments were affixed to plastic rods (or "filaments handles") which were cut to the approximate length of a pencil for ease of handling and comfortable fit in the therapist's hand. The devices were known as "aesthimometers". The advantage of these new filaments, when affixed to a plastic rod, was their ease of handling and their ability to create a range of testing values by varying the diameter of the filament affixed to a rod. These monofilaments attached to plastic rods with glue came to be known as "Semmes-Weinstein monofilaments" and became the standard means for repeatable testing and measurement of the threshold of cutaneous sensory perception. In addition to nylon, monofilaments have also been made of materials such as steel and nitinol.

In the conventional approach of testing diabetic foot, the clinician would contact the foot with different force levels in generally 7 to 10 different places with the monofilaments. The testing is to determine whether the patient has sense in that area. Examination using monofilaments, and testing pinprick sensation in general, has disadvantages as the current methods of testing are prone to inter-investigation variation due to the pressure applied. For example, whereas a general force of 10 grams should be applied to gauge sensation, which can be determined when the monofilament bends, the extent of the bending of the monofilament can vary from clinic to clinic and clinician to clinician. Further, current testing with monofilaments is rather spatial in terms of the points contacted on the foot. Due to human limitations, the clinician often does not have the ability to accurately test more points on the foot. Still more, the clinician likely cannot track a specific nerve on the foot in order to track its degradation. Further, there is no comparison of test results with previous test results conducted at the similar if not at the same location to determine degradation of the nervous system. Also, it is not accurate to determine the palpation force based on the bending of the filament, which at best is qualitative.

It is an object of the present system to overcome the disadvantages and problems in the prior art.

DETAILED DESCRIPTION

The present invention proposes to use an automatic system for systematically actuating the palpation process so that the test can achieve accuracy and consistency, acquiring additional info from increasing the number of palpation points, and recording and documenting the test results for later reference/use.

These and other features, aspects, and advantages of the apparatus and methods of the present invention will become better understood from the following description, appended claims, and accompanying drawings where:

The following description of certain exemplary embodiment(s) is merely exemplary in nature and is in no way intended to limit the invention, its application, or uses. Throughout this description, the term "test" is used interchangeably with the term "diagnostic" in referring to a method of determining the nature of the case of a disease.

The term "automated" refers to the use of electronic systems to replace human operators, however human operators continue to have control over the electronic systems, such as during programming and monitoring.

The term "palpation" refers to the application of an object with pressure to the mammalian body portion for the purpose of diagnoses.

Figure 1:
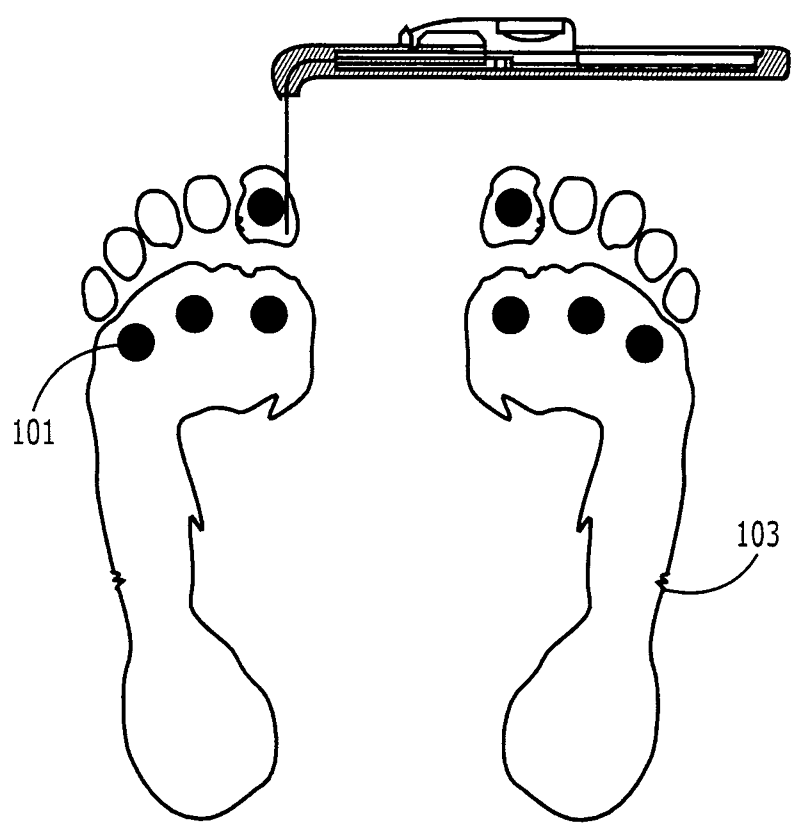
FIG. 1 shows an example of the prior art method of monofilament testing.

Now, to FIGS. 1-5,

FIG. 1 is an example of the spatial nerve of prior art method of testing diabetic foot. As shown, the prior art generally focused on four points 101 on a patient's foot 103. The drawbacks of such a spatial arrangement include an inability for early detection of nerve degradation, as well as missing particular contact points on the foot.

Figure 2:
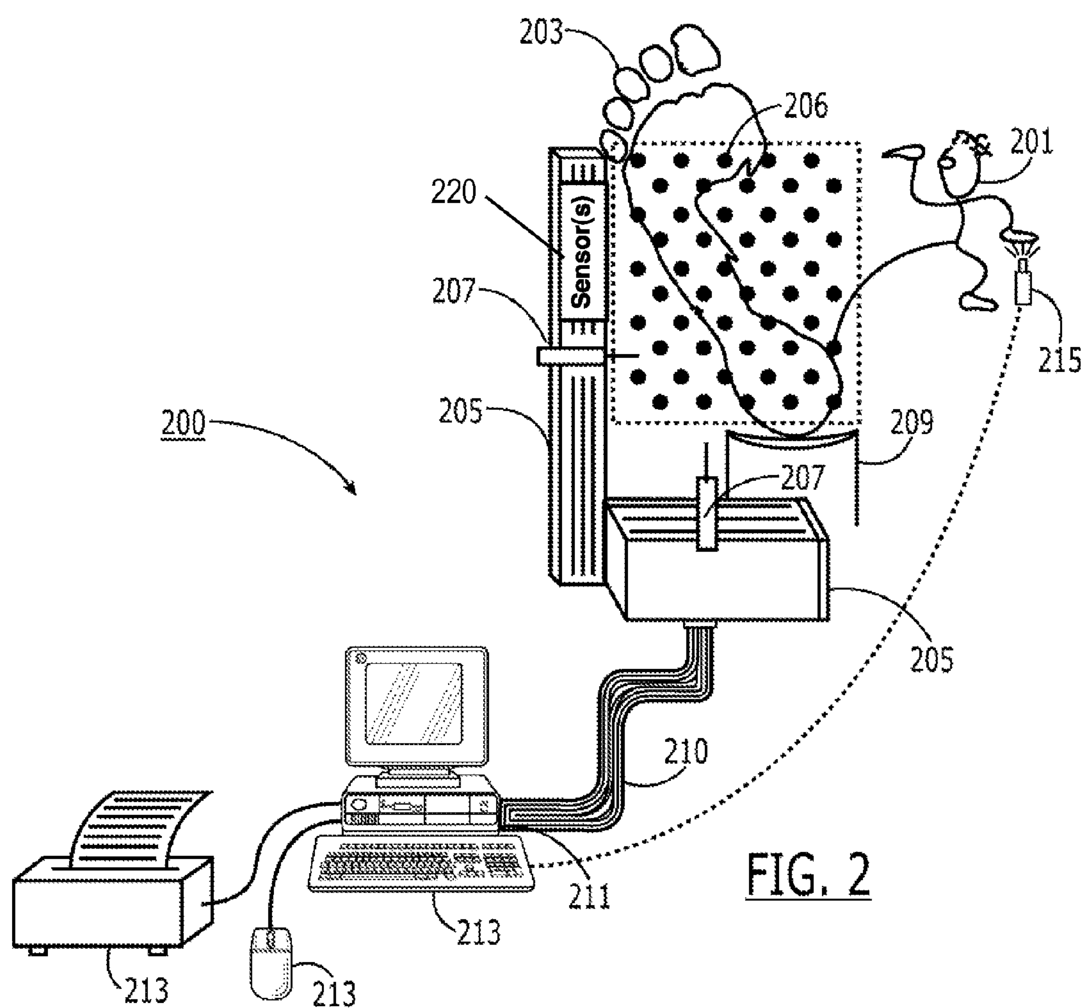
FIG. 2 shows a system of the present invention.

FIG. 2 is a system 200 of the present invention, comprising a robotic device 205 upon which actuating elements 207 are positioned thereon, a resting portion 209 to accommodate the foot 203 of a patient 201, a controller 211, user interface devices 213, a feedback device 215, and a spatial array 206. The system 200 is useful for performing automated foot testing.

The system 200 is suitable for use by patients 201 afflicted with trauma affecting continuity of nerve fibers such as leprosy, stroke, diabetes, multiple sclerosis, diseases resulting in diminished nerve conductivity, and nerve compression syndromes. In one embodiment, the system 200 is for use by patients 201 in risk of or afflicted with diabetes. In particular, the patients 201 are at risk of developing diabetic neuropathy which metastasizes itself in the foot 203 of the patient 201. The system 200 includes a rest portion 209 by which the patient 201 may relax his foot 203 during testing.

The system 200 also includes a robotic device 205 for providing the means by which the test is administered. The robotic device 205 can be a Cartesian robot system or a Gantry-type robotic system, whereby it operates in the planes of x, y, and/or z. The robotic device 205 can have at least 2 degrees of freedom, including vertical movement, extension and retraction, and rotation traverse in the Y direction. The robotic device 205 can contain one or more sensors 220, including but not limited to some positioning sensors, for example laser distance movement, visual/camera sensors, to position the foot resting on the foot rest, and some force sensors, for example pressure transducers, to sense how much force is being applied by the actuator element. The sensors allow the robotic device 205 to calculate its position in space relative to the patients foot 203, and monitor changing conditions during testing.

The robotic device 205 also contains equipment necessary for operation, including but not limited to gears, servos, power supply, antennas, lubricant, tracks, belts, etc. and electronic devices including fuses, resistors, switches, capacitors, actuator buttons, and the like. The robotic device 205 may further contain communication means 210 allowing it to be programmed and/or controlled by direct link or remote link. Such communication means 210 can include antennas, cables, optical link, radio link, satellite devices, connectors, and the like. The robotic device 205 may also contain on-board operation means, such as on-off switches, display, controller buttons, and safety switches. The robotic device 205 may also contain memory storage, such as RAM or ROM. In one embodiment, the robotic device 205 is a SCARA (Selective Compliant Articulated Robot Arm) capable of operating in planes x, y, and z. In another embodiment, the robotic device 205 is capable of operating in a x plane and a y plane.

Mounted onto the robotic device 205 are actuating elements 207, such as motors, solenoids, or electric pulse devices possessing monofilament, pins or needles. The pins, needles, or monofilaments can range from slightly shift to shift states. The pin, monofilament, or needle is preferable disposable being used a few times and discarded. The elements 207 are attached such that they move in the x, y, and/or z plane in concert with the robotic device 205. The elements 207 are, in essence, electromechanical devices that contain a coil would around a movable core. As will be discusses later, the actuating elements 207 produce a magnetic flux which induces the core to move. As will also be discussed later, the core of the elements 207 can be a pin, monofilament, or needle, said core which contacts the foot of the patient. In one embodiment, the core is a needle. The elements 207 extend from the robotic device in a staggered manner, i.e., the elements 207 positioned on the robotic devices 205 Y-axis is extended more than the elements 207 positioned on the X-axis, or vice versa. In one embodiment, there is at least one element 207 on the robotic devices 205 Y-axis and one element 207 on the X-axis. In another embodiment, multiple elements may be present on the X-Y plane.

The robotic device 205, and correspondingly the actuating elements 207, may be connected to and controlled by a controller 211. As previously mentioned, connection may be through a connection means 210. The controller 211 can contain processors, which include microprocessor, temporary registers, accumulators, holding registers, and logic units, memory, including ROM, RAM, and removable memory, and User Interface Devices (UIDs) 213, including displays, keyboards, mouse', and printers. As a general note, the processor is capable of providing output or control signals in response to input signals from a UID, e.g., displayed on the display 213 which may be a touch sensitive screen, executing instruction stored in the memory, and the like. UIDs 213 allow the clinician to interact with the controller 211.

The memory of the controller 211 may have stored thereon routines, subroutines, and data suitable for programming and controlling the robotic device 205. Algorithms may also be stored on the memory, such as analyzation algorithms, data organization algorithms, and the like. As will be further discussed, the routines also include algorithmic functions that instruct the robotic device 205 to perform in accordance with the instant invention. Subroutines allow the overlying algorithmic functions to be modified, such as by setting a particular pattern for the robotic device 205 to follow during operation. Data can include patient health records, historical data, statistical data, and the like. The data should be able to be drawn upon, i.e., analyzed by the clinician when diagnosing the patient.

The patient can also engage the controller 211, usually by delivering feedback to the controller 211 via a feedback device 215. The feedback device 215 is actuated by the patient in response to sensing stimulation during testing. Suitable feedback devices 215 include actuator device with a button, switching device, auditory-sensing device, and the like. The feedback device 215 can communicate with the controller 211 via direct cable link or wireless communication means such as radio frequency (RF), wifi, satellite, or technologies such as Bluetooth™.

Examples of suitable controllers 211 include personal computers, laptops, PDAs, and control panels. The UIDs 213 may be implemented in the controller 211 or separated therefrom.

The system 200 also includes an array 206. The array 206 is preferably abstract, as opposed to a physical manifestation placed on the foot. The array 206 sets forth the contact points on the foot to be tested by the monofilament solenoid 207. The array 206 may be an unlimited number of contact points, however generally ranging from 4 to 10000 points, preferably from 10 to 1000, more preferably 20 to 500 points. However, the actually number of points may vary depending on the size of the patient's foot, i.e., the larger the foot, the more number of points. In comparison to the prior art, the array of the present invention is much less spatial, allowing for the tracking of nerves and nerve degradation. As will be discussed later, the array 206 can be created by algorithms stored on the controller 211. The element 207 then administers the diagnostic in accordance with the created array 206. The array 206 may also be created using data obtained from the sensing devices of the robotic device 205.

Figure 3:
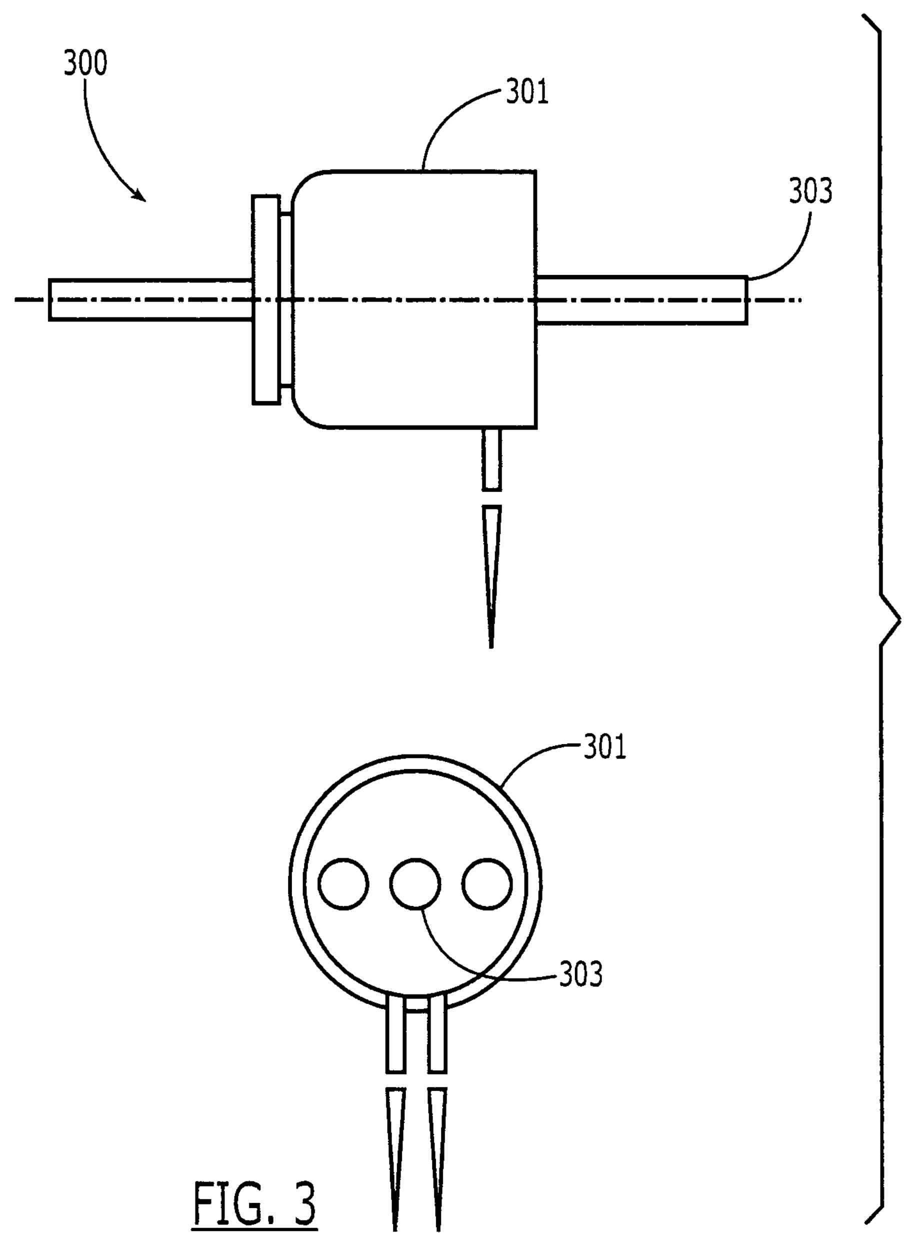
FIG. 3 is an example of the actuating element to be used in the instant invention.

FIG. 3 is an actuating element 300 used in accordance with the present invention, comprising a case 301 with a core 303. The actuating element can be a motor associated with a mechanical system, solenoid, or an electric pulse device. In the case where the core 300 is a solenoid, the solenoid can be a tubular solenoid, linear solenoid, push-pull solenoid, push solenoid, rotary solenoid, plunger-type solenoid, or soft shift solenoid. In one embodiment, the element is a push-type solenoid. The element 300 may operate under DC power or AC power. In the event the element 300 operates under AC power, a rectifier can be connected therewith for smooth performance. In one embodiment, the core 303 is a needle. In one embodiment, the actuating element 300 is an electromechanical actuator where by the force can be controlled during palpation, in such an embodiment, palpation is performed with a force/pressure transducer, whereby the palpation is controlled by the measured force so that one contact point may have 10 gm (gram-force) of pressure applied and another contact point may have 20 gm of pressure applied. In the case of an electromechanical actuator, one contact point may have several different pressures applied, for example 10 gm, 20 gm, 25 gm, or 30 gm applied in progression until the patient feels sensation.

The case 301 can include a coil, flux path, bore hole (for allowing movement of the core 303), and stop. The case 301 may be sized to allow proper fitting on the robotic device, as previously discussed.

The core 303 is positioned within the case 301. The core 303 can be a strand of material, such strand of material being of a thickness to allow deliverance of a desired force to the foot of the patient before failure of the strand. The core 303 can be designed to deliver a force in the range of from about 2 gm to 40 gm. The diameter size can be dependent on the force as, if it is desired to deliver a particular force, the diameter size should increase to deliver the desired force. This will ensure the desired force is administered in full to the patient's foot before failure of the core, i.e., the core bends before the full force is administered.

The core 303 can be made of a material suitable for use in the solenoid following powering the solenoid (such powering creating an electromagnetic field). Suitable materials include metal-metallic alloys made of from about 80% transition metals selected from the group consisting of Fe, Co, or Ni, and a metallic component selected from B, C, Si, P, or Al. Examples of materials include $FeOFe_2O_3$, $NiOFe_2O_3$, $CuOFe_2O_3$, $MgOFe_2O_3$, MnBi, MnSb, $MnOFe_2O_3$, $Y_3Fe_2O_{12}$, $CrO_2$, MnAs, Gd, Dy, and EuO.

In operation, the core 303 is positioned within the case 301 to create the actuating element 300. When the element 300 is energized, the core 303 will be extended. The element 300 should be energized to the extent that the core 303 will provide a certain force to a contact point on the patient's foot. After the full desired force has been administered, the power to the element 300 will be reduced or decreased, as in through the use of an adjustable power means such as an adjustable resistor, thus withdrawing the core 303 back into the bore hole. Concomitant with the application of full force, the patient will provide feedback to the controller as to whether or not he felt contact from the element 300. When a needle is used as the core, it is not required that the needle bend upon compression.

The core 303 can be removed and replaced with cores of different materials and strengths, allowing for higher or lower forces.

Figure 4:
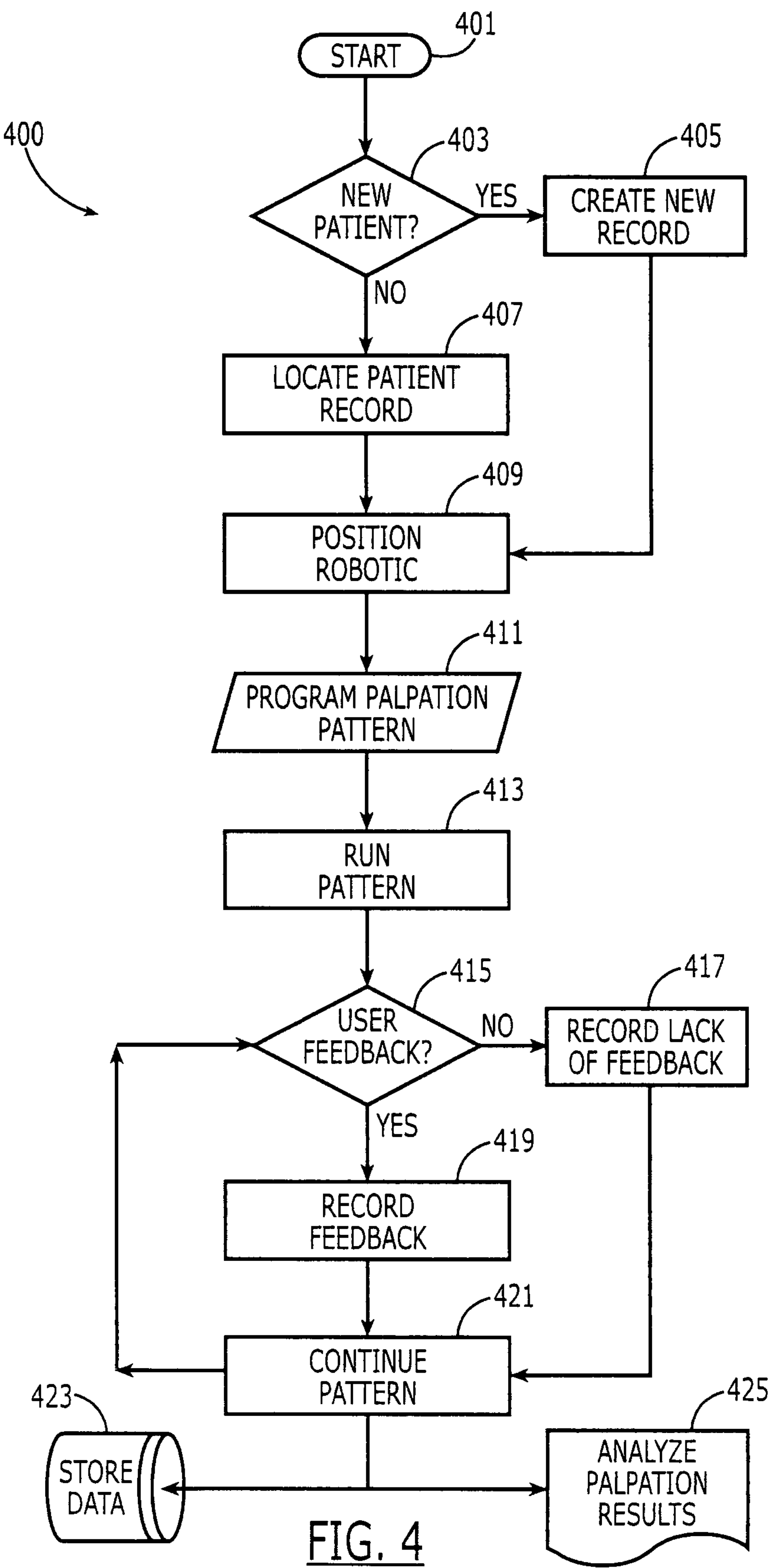
FIG. 4 is an example of an operational algorithm suitable for the present invention.

FIG. 4 is an example of an operation algorithm 400 that may be used to control the robotic device and hence the application of the actuating elements of the present invention. The algorithm 400 may be stored on the memory of the controller. Through the programming and control of the robotic device, contact from the solenoids can be made in specific locations on the patient's foot, each contact adhering to an array designed through the controller. This algorithm 400 thus allows for the automated foot testing in a detailed manner. The algorithm 400 can be modified from this example without deviating from the general purpose, which is the automation of foot testing in a palpation patterned method.

The algorithm 400 may first be started 401 by logging onto the controller or turning on the controller. The algorithm 400 can first determine whether the patient is new 403 by requesting this information from the clinician. In the event the patient is new, i.e., first time having the test administered in that hospital or clinic, a new record can be created 405. Creating a new record 405 can consist of asking general patient questions, such as name, age, sex, race, history of health, and more specific questions to the current state of the patient's foot, including but not limited to current foot ulcers, claw toe uniformity, foot shape, elevated skin temperature, ankle dorsiflexion, toenail health, callous build-up, ankle muscle weakness, pedal pulse, and shoe shape. In the event the patient is not new, the patient's record can be located 407 on the memory of the controller on a removable memory source.

Following, the creation 405 or location 407 of a patient's record, the positioning of the robotic device 409 for performing the diagnostic may be performed. Positioning the robotic device 409 can include the steps of changing core of the actuating element readjustment of the actuating element on the robotic device, moving the robotic device, placing the patient's foot on the foot rest, positioning the monofilament actuating element directly in front of the patient's foot, and the like. As different patient's feet are of a different size, positioning can include the robotic device moving within the x, y, and/or z planes to ensure it is at an appropriate height and distance to administer the test. Determining the appropriate height and distance involves being at a height and distance where the core can exert full force at full extension upon a contact point on the patient's foot, and at the same time ensuring that the actuating element is not so close that it punctures or wounds the patient's foot. Further, the puncture point should avoid ulcers, calluses, and scars. As discussed earlier, the robotic device can contain sensors. The sensors can be used to assist in appropriately positioning the robotic device 409, for example a laser sensor can allow the robotic device to determine its distance from the patient's foot, the size of the patient's foot, etc. The information from the sensors may be passed to the controller for further uses.

Following positioning the robotic device 409, a palpation pattern may then be programmed 411 into the controller. The palpation pattern will be used to control the movement of the robotic device, and hence the actuating element, during the diagnostic administration. The palpation pattern will be designed in the X-Y plane. In a preferred embodiment, the palpation pattern will consist of two contact points or more to be tested in succession, without intervention from the clinician. Thus, the diagnostic will operate in an automated manner. The palpation pattern is preferably less spatial, in comparison to the prior art, wherein at least 7 to 10 points on the patient's foot will be contracted with the core. In a preferred embodiment, a minimum of 15 contact points will be created by the array. The palpation pattern can also include force variables for specific contact points, therefore allowing different contacts on the patient's foot to be tested with different forces. Programming the palpation pattern 411 may occur by the clinician accepting a preprogrammed pattern stored on the controller, the clinician designing a palpation pattern based upon contact points he believes should be tested, or the controller designing a pattern based upon information entered into the controller and/or based upon previous diagnostic performed on the patient, such diagnostic results being stored on the controller. The palpation pattern may also be programmed to allow two or more contact points to be tested simultaneously.

During testing the patient can provide feedback 419 to the controller and/or clinician as to the sensations felt during the diagnostic. As discussed previously, feedback 419 can occur via feedback devices such as actuator buttons, auditory feedback, visual feedback including hand signs, and the like. If, following contact with the core, feedback is not received, this lack of response will be recorded 417. If feedback is received, this response is recorded 419. The feedback is delivered to the controller and stored on the memory of the controller.

The palpation pattern will continue 421 to run until its termination, i.e., the pattern has been gone through in its entirety. Of course, the pattern may be ceased prior to it completion by the clinician or controller if desired or an emergency presents itself.

The feedback received can then be stored on the memory of the controller 423 for association with the palpation pattern and with the patient's record. The feedback may also be stored on a removable memory, such as flashdisk, to allow the patient to transport the data to another clinic. The feedback may also be fed into analyzing algorithms 425 to allow comparison the data to the patient's previous diagnostics and against historical medical data. The feedback may also be printed in hardcopy, allowing the clinician to discuss results of the diagnostic with the patient.

Figure 5:
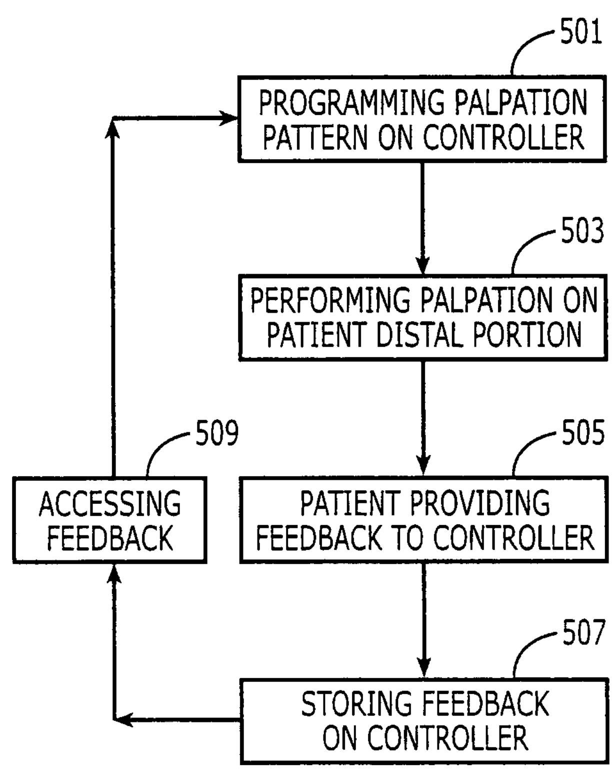
FIG. 5 shows a method of an automated palpation testing.

FIG. 5 is a method of automated palpation testing performed in accordance with the present invention, including the steps of programming a palpation pattern on a controller 501, performing palpation of a patient's distal portion, such as a hand or foot, 503, having the user provide feedback to the controller 505, and storing the feedback on the controller for future use 507.

As stated previously, programming a palpation pattern consists of directing the future movements of the robotic device, and hence the attached actuating element, in an X-Y plane. Programming can be performed by the clinician, interacting with the controller through the UIDs, or the controller designing a palpation pattern that can be based upon previous test results. In an example, the clinician can interact with the controller by using a joystick to pinpoint contact points on a graphical picture of the patient's foot. Programming can include multi-variables, including using multiple forces applied during the tests, using two or more cores to contact the foot at the same time, setting a high number of contact points on the array which would allow the tracking and monitoring of specific nerves, using a combination of x and y coordinates to vary the contact points, and the like.

Performing palpation on a patient's distal portion 503 is performed in an automated manner, i.e., points on the patient's foot are contact one after the other without input or direction from the clinician. Through the various sensors, the controller will ensure the robotic device is at a sufficient distance to effectuate the proper force while not harming the patient's distal portion.

Concomitant with performance of the palpation test 503, the patient provides feedback to the controller 505. The feedback is used to gauge whether sensation was felt by the patient following contact at a specific point. The feedback can be delivered through a feedback device to the controller. Feedback not only determines whether there is sensation in a specific location, but also the progression of the degradation of a particular nerve. The feedback can be stored 507 on the controller and associated with the patient's record. The feedback can also be accessed by the controller for incorporation into future palpation patterns. Further, the feedback can be analyzed and used for discussion with the patient.

Having described embodiments of the present system with reference to the accompanying drawings, it is to be understood that the present system is not limited to the precise embodiments, and that various changes and modifications may be effected therein by one having ordinary skill in the art without departing from the scope or spirit as defined in the appended claims.

In interpreting the appended claims, it should be understood that:

a) the word "comprising" does not exclude the presence of other elements or acts than those listed in the given claim;

b) the word "a" or "an" preceding an element does not exclude the presence of a plurality of such elements;

c) any reference signs in the claims do not limit their scope;

d) any of the disclosed devices or portions thereof may be combined together or separated into further portions unless specifically stated otherwise; and e) no specific sequence of acts or steps is intended to be required unless specifically indicated.

The invention claimed is:

1. A system for automated mammalian distal portion testing, comprising:

(i) a robotic device configured to move across a three-dimensional contact point array in a pre-programmed palpation pattern, wherein the three-dimensional contact point array defines a plurality of contact points of the mammalian distal portion and is configured to track nerves and nerve degradation in the mammalian distal portion; wherein the mammalian distal portion is selected from the group consisting of a hand and a foot;

(ii) at least two actuating elements positioned on an X-Y plane of the robotic device configured to move in concert with the robotic device and make contact, without obstruction, with the plurality of contact points of the mammalian distal portion, wherein the at least two actuating elements each comprise an extendable core to provide a force to a contact point on the mammalian distal portion; wherein at least two contact points of the mammalian distal portion are contacted simultaneously;

(iii) a resting portion for accepting the mammalian distal portion;

(iv) a controller connected to the robotic device that is configured to control movement of the robotic device and movement of the at least two actuating elements;

(v) one or more user interface devices controllably attached to the controller; and (vi) a feedback device configured to provide feedback information of the testing of the mammalian distal portion to the controller received from the mammal being tested, wherein the feedback information is associated with a coordinate of a specific contact point when the feedback information is provided.

2. The system of claim 1, wherein the mammalian distal portion is the foot.

3. The system of claim 1, wherein the mammalian distal portion is of a mammal afflicted with trauma affecting continuity of nerve fibers, wherein such trauma is selected from the group consisting of leprosy, diabetes, stroke, multiple sclerosis, diseases resulting in diminished nerve conductivity, and nerve compression syndromes.

4. The system of claim 1, wherein the robotic device comprises one or more sensors.

5. The system of claim 1, wherein the at least two actuating elements are selected from the group consisting of (i) a solenoid comprising a monofilament, a pin or a needle, (ii) a motor with a mechanical-system comprising a monofilament, a pin or a needle, and (iii) an electric pulse device comprising a monofilament, a pin or a needle.

6. The system of claim 5, wherein the at least two actuating elements are monofilament solenoid solenoids selected from the group consisting of a tubular solenoid, a linear solenoid, a push-pull solenoid, a push solenoid, a rotary solenoid, a plunger type solenoid, and a soft shift solenoid.

7. The system of claim 1, wherein the robotic device further comprises:

(vii) a communication means.

8. The system of claim 1, wherein the controller is selected from the group consisting of a personal computer, a laptop, a personal digital assistant (PDA), and a control panel.

9. The system of claim 1, wherein the user interface device is selected from the group consisting of a display, a printer, a keyboard, and a mouse.

10. The system of claim 1, wherein the array comprises from 4 to 10,000 contact points.

11. The system of claim 1, wherein the controller comprises an operation algorithm stored therein.

12. The system of claim 1, wherein the robotic device is driven by one of the mechanisms selected from the group consisting of an electromechanical mechanism, a pneumatic mechanism, and a hydraulic mechanism.

13. The system of claim 1, wherein the core is a monofilament, a pin, or a needle.

14. The system of claim 1, wherein the robotic device is configured to perform a movement selected from the group consisting of vertical movement, extension, retraction, and rotation traverse in a y plane.

15. The system of claim 1, wherein the at least two actuating elements are configured to produce a magnetic flux which induces the extendable core to move.

16. The system of claim 1, wherein the plurality of contact points of the mammalian distal portion ranges from 4 to 10,000 points.

17. The system of claim 1, wherein the at least two actuating elements each further comprise a case surrounding the extendable core.

18. The system of claim 17, wherein the case comprises a means for moving the core selected from the group consisting of a coil, a flux path, a bore hole and a stop.

19. The system of claim 1, wherein the at least two actuating elements are configured to move in an X-Y-Z plane in concert with the robotic device.

20. A method of automated testing of a mammalian distal portion, the method comprising the steps of:

(a) starting a controller;

(b) determining whether the mammal has a record;

(c) positioning a robotic in front of the mammalian distal portion, wherein the robotic device comprises at least two actuating elements on an X-Y plane of the robotic device and wherein the at least two actuating elements each comprise an extendable core to provide a force to a contact point on the mammalian distal portion; wherein the mammalian distal portion is selected from the group consisting of a hand and a foot;

(d) moving the robotic device across a three-dimensional contact point array on the mammalian distal portion in which the three-dimensional contact point array defines a plurality of contact points of the mammalian distal portion and is configured to track nerves and nerve degradation in the mammalian distal portion; wherein at least two contact points of the mammalian distal portion are contacted simultaneously;

(e) programming a movement of the robotic device and a palpation pattern of the at least two actuating elements on the controller;

(f) performing the movement of the robotic device and the palpation pattern of the at least two actuating elements on the mammalian distal portion;

(g) receiving feedback information from the mammal being tested in response to the palpation diagnostic testing;

(h) associating the feedback information with a coordinate of a specific contact point when the feedback information is provided;

(i) storing the feedback information; and (j) accessing the feedback information when further diagnosing the mammal.

21. The method of claim 20, further comprising the step of:

(k) analyzing a palpation testing result after the feedback information is received.

22. The method of claim 20, wherein positioning the robotic device comprises the step of determining height and distance between the at least two actuating elements and the mammalian distal portion.

23. The method of claim 20, wherein programming the palpation pattern occurs by a clinician accepting a preprogrammed pattern stored on the controller, a clinician designing a palpation pattern, or the controller designing a palpation pattern based upon previous diagnostic performed on the mammal.

24. The method of claim 20, wherein performing the palpation diagnostic comprises contacting two or more contact points on the mammalian distal portion in immediate succession using a force of between 2 mg to 40 gm.

25. The method of claim 24, wherein the performing of the palpation diagnostic occurs by the robotic device adhering to the three-dimensional contact point array.

* * * * *